(12) United States Patent
Lindgren et al.

(10) Patent No.: US 6,728,579 B1
(45) Date of Patent: Apr. 27, 2004

(54) "MEDICAL ELECTRODE LEAD"

(75) Inventors: Anders Lindgren, Täby (SE); Mona Heqg, Stockholm (SE)

(73) Assignee: St. Jude Medical AB, Järfälla (SE)

( * ) Notice: Subject to any disclaimer, the term of this patent is extended or adjusted under 35 U.S.C. 154(b) by 0 days.

(21) Appl. No.: 09/937,257

(22) PCT Filed: Mar. 7, 2000

(86) PCT No.: PCT/SE00/00449
§ 371 (c)(1),
(2), (4) Date: Sep. 21, 2001

(87) PCT Pub. No.: WO00/56396
PCT Pub. Date: Sep. 28, 2000

(30) Foreign Application Priority Data

Mar. 22, 1999 (SE) .............................. 9901032

(51) Int. Cl.$^7$ ................................ A61N 1/05
(52) U.S. Cl. ........................ 607/116; 607/119
(58) Field of Search ............... 607/116, 119, 607/122; 600/373, 374, 377, 585

(56) References Cited

U.S. PATENT DOCUMENTS

| | | | | |
|---|---|---|---|---|
| 4,739,768 A | | 4/1988 | Engelson | 128/658 |
| 4,771,788 A | * | 9/1988 | Millar | 600/455 |
| 4,791,939 A | * | 12/1988 | Mallard | 606/129 |
| 5,170,787 A | | 12/1992 | Lindegren | 128/642 |
| 5,487,757 A | | 1/1996 | Truckal et al. | 607/122 |
| 5,571,160 A | | 11/1996 | Nyman | 607/122 |
| 5,593,433 A | * | 1/1997 | Spehr et al. | 607/128 |
| 5,728,148 A | | 3/1998 | Boström et al. | 607/116 |
| 5,833,604 A | | 11/1998 | Houser et al. | 600/373 |
| 6,544,197 B2 | * | 4/2003 | DeMello | 600/585 |

FOREIGN PATENT DOCUMENTS

| | | | |
|---|---|---|---|
| EP | 0 823 261 | 2/1998 | A61M/25/09 |
| EP | 0 823 264 | 2/1998 | A61N/1/05 |

* cited by examiner

Primary Examiner—Carl Layno
(74) Attorney, Agent, or Firm—Schiff Hardin LLP

(57) ABSTRACT

A member for modifying the stiffness of a cardiac electrode lead is flexible and elongated and contains a longitudinal cavity extending along the member. The member has an interior cross-sectional dimension defined by the cavity and an exterior cross-sectional dimension allowing the member to be withdrawably positionable in a channel of an electrode lead. The interior cross-sectional dimension of the member allows a guide wire to be movable therein. The extent of the guide wire disposed in the cavity allows selective setting of the stiffness of the member, and therefore the stiffness of the electrode lead in which the member is disposed.

14 Claims, 2 Drawing Sheets

HEART-STIMULATING DEVICE

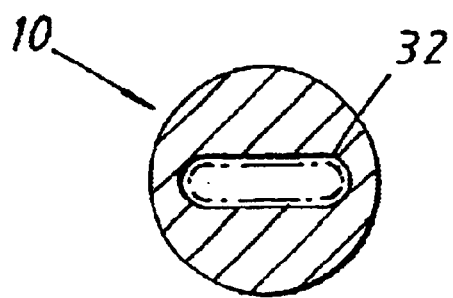
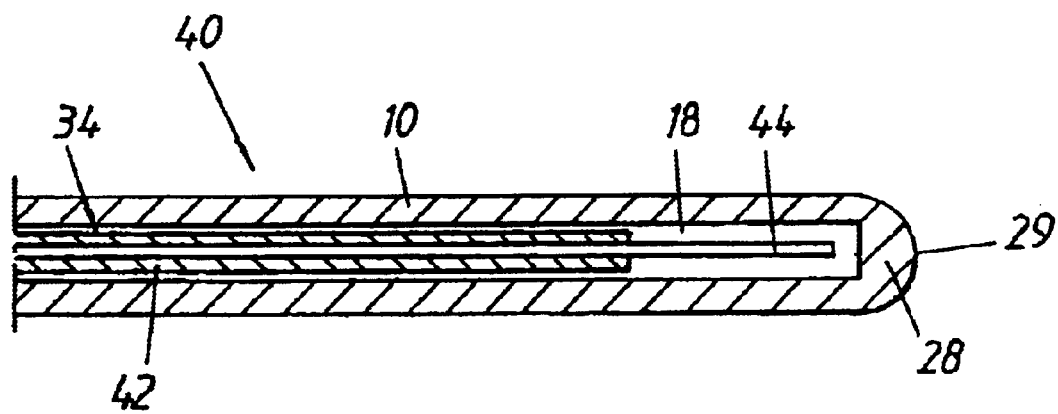

"MEDICAL ELECTRODE LEAD"

BACKGROUND OF THE INVENTION

1. Field of the Invention

The present invention relates to heart electrode leads of the kind having a proximal end to be connected to a heart-stimulating device and a distal end insertable via the vascular system into the human or animal heart. This kind of heart electrode lead is particularly suitable for intracardial stimulation of the heart with the help of an implantable pacemaker or defibrillator.

2. Description of the Prior Art

A large number of different heart electrode leads are known in the art. Such electrode leads have to fulfil many different requirements. One requirement is that the electrode lead is sufficiently flexible once it has been implanted in the human or animal body, such that it does not exert stress on or injure the body parts surrounding the implanted electrode lead. Another requirement is that the electrode lead is sufficiently rigid so that it may be inserted, for example via the vascular system, into a human or animal heart. Furthermore, it is sometimes required that the distal end of the electrode lead may be guided, during the insertion, to a specific position in the heart.

U.S. Pat. No. 5,487,757 describes a multicurve deflectable catheter. The catheter has an axial lumen in which a stiffener wire is slidably introduced. The stiffener wire, when advanced into a tip portion of the catheter, will give the tip portion and the stiffener wire a combined bending stiffness in order to give the tip portion a certain radius of curvature. The catheter may further include a core wire configured to rotate the deflectable tip about a longitudinal axis. The catheter further has a manipulator wire coupled to the distal end of the deflectable tip, whereby the deflectable tip may be deflected by axial force applied to the manipulator wire. The manipulator wire, the stiffener wire and the core wire are located in separate cavities arranged side by side at the tip portion. As a consequence of this arrangement, the flexibility of the catheter will depend on in which direction the catheter is bent.

U.S. Pat. No. 5,571,160 describes an electrode cable for use with a pacemaker. A tubular element can be slid on and off the electrode cable in order to impart a certain curvature onto the electrode cable. The electrode cable may be straightened by means of a stylet introduced into a channel of the electrode cable.

U.S. Pat. No. 5,170,787 describes a device for simplifying the positioning of electrodes inside living bodies. This device comprises a hollow lead in which a stylet wire combination is inserted. The stylet wire combination comprises an outer tubular member and an inner wire member. The inner wire member may have a preshaped curvature. By withdrawing the outer tubular member a certain distance, the inner wire member causes the distal end of the lead to take a curved shape caused by the curvature of the inner wire member.

Although it is possible to modify the stiffness of the above described electrode leads by withdrawing or inserting the different stiffening members, there is still a need to make it possible to further modify the stiffness of the electrode leads. In particular, it has been found that, when the electrode lead is being inserted into a human or animal body, it is sometimes desirable to withdraw the stiffening wire to a certain extent when the distal end of the electrode lead passes certain positions in the body. When the stiffening wire is withdrawn, it has been found that the portion of the electrode lead from which the stiffening wire has been withdrawn is sometimes too flexible. It should be noted that it is an advantage that the electrode lead is flexible once it has been inserted into its predetermined position in the body. Also during the insertion phase, it is sometimes an advantage that the electrode lead is very flexible in order to allow for a portion of the lead to be bent. One example when it is of interest to partly withdraw the stiffening wire is when the distal end of the electrode lead is introduced into the heart of a patient. However, when the stiffening wire is withdrawn, the distal end of the electrode lead may be too soft so that it is difficult to steer this end into position in, for example, the ventricle. Instead, the distal end of the electrode lead may have a tendency to follow the blood stream into the pulmonary artery.

SUMMARY OF THE INVENTION

It is an object of the present invention to provide a heart electrode lead in which the stiffness may be modified even when a guide wire is partly or totally withdrawn from the electrode lead.

This object of the invention is obtained by a member for modifying the stiffness of a heart electrode lead having a proximal end to be connected to a heart-stimulating device and a distal end insertable via the vascular system into a human or animal heart, the member being flexible, elongated and having a longitudinal cavity extending along said member, the member having an interior cross-sectional dimension defined by the cavity and an exterior cross-sectional dimension, the exterior cross-sectional dimension being such that the member is withdrawably positionable in a channel of the elongated heart electrode lead, and the interior cross-sectional dimension being dimensioned to allow a guide wire to be movably arranged therein.

When the member is positioned in the electrode lead, the electrode lead will be more stiff and thus less flexible. The member may thus be located in the electrode lead when the electrode lead is inserted via the vascular system into the heart. Even when no guide wire is positioned in the electrode lead, or when the guide wire is partly withdrawn, the distal end of the electrode lead will have a certain stiffness which makes it easier to position the distal end of the electrode lead at a certain position in the heart.

In a further embodiment of the invention, the outer boundary of the cross-section of the member is essentially circular. The member thereby fits into a corresponding circular channel in the electrode lead. Furthermore, since the cross-section is circular, the member and the electrode lead may be arranged concentrically such that the flexibility of the electrode lead will be independent of the direction into which the electrode lead is bent.

According to a further embodiment, the member is made of a non-metallic material. Such material will make it possible to make the member such that it is neither too stiff, nor too soft.

According to another embodiment of the invention, the material is a polymer. Such a material is particularly advantageous in order to give the member a suitable stiffness.

According to still another embodiment of the invention, an arrangement is provided at one end of said member for preventing the end of the guide wire from passing the end of the member. This embodiment has the advantage that the position of the member in the electrode lead may be modified by pushing said member with the help of a guide wire.

Furthermore, according to this embodiment there is no risk that the guide wire extends beyond the end of the member.

According to still another embodiment of the invention, at least a portion of the member has a pre-set curvature. Since the member has a pre-set curvature, the electrode lead will tend to be bent according to this curvature. This makes it possible to position the distal end of the electrode lead at a certain position in the heart.

According to another preferred embodiment of the invention, the longitudinal cavity has an essentially circular cross-section and is adapted to allow a guide wire having a corresponding cross-section to be movably arranged therein. By this arrangement, the guide wire, the member and the electrode lead may be arranged concentrically such that the flexibility of the lead is the same in all bending directions.

According to still another embodiment of the invention, the longitudinal cavity has an elongated cross-section and is adapted to allow a guide wire having a corresponding cross-section to be movably arranged therein. Such an embodiment is advantageous if the flexibility is to be different in different bending directions of the electrode lead. This is, for example, the case when the distal end of the electrode lead is supposed to bend in a certain direction in order to make it easier to position the distal end of the electrode lead at a certain location in the heart.

The invention also provides an elongated heart electrode lead adapted for insertion via the vascular system into the human or animal heart, the heart electrode lead having a proximal end to be connected to a heart-stimulating device and a distal end having one or more electrode surfaces adapted to be inserted into the heart, the electrode lead having at least one electrical conductor adapted to electrically connect the heart-stimulating device to the electrode surfaces, a channel extending from the proximal end to a position at or close to said distal end, and a member according to any one of the above embodiments, positioned in the channel, the member being movably arranged in the longitudinal direction in the channel and the member being arranged such that it may be withdrawn from the channel via the proximal end.

According to the invention, there is also provided a guide wire arrangement adapted to be movably positioned in a channel in an elongated heart electrode lead having a proximal end to be connected to a heart-stimulating device and a distal end having one or more electrode surfaces to be inserted into a human or animal heart, the guide wire arrangement having a member according to any one of the above-mentioned embodiments, and an elongated guide wire movably arranged in the longitudinal cavity. According to this aspect of the invention, a guide wire arrangement suitable to be positioned in a channel in an elongated heart electrode lead is provided.

According to a preferred embodiment, the guide wire is a single elongated element. Such a guide wire is relatively easy to produce and, furthermore, can be made with a relatively small diameter such that it easily fits into the longitudinal cavity of the mentioned stiffness-modifying member.

According to a further embodiment, at least a portion of said guide wire has a pre-set curvature. By this measure, the electrode lead may take a corresponding pre-set curvature, whereby the distal end of the electrode end may be positioned at a predetermined location in the heart.

According to a further embodiment, the guide wire has an outer elongated tubular element movably arranged in the longitudinal cavity and an inner elongated element movably arranged in the tubular element. By such a double guide wire arrangement, the stiffness of the electrode lead may be modified further. Furthermore, the curvature of the electrode lead may be controlled more precisely by such a double guide wire arrangement. It should be pointed out that the tubular element does not, necessarily, have to have a circular cross-section. The cross-section may, for example, be elongated.

According to still another embodiment, the inner element has a preset curvature. The outer tubular element of the guide wire may be made to be stiffer than the inner element. Thereby the guide wire, and thereby the electrode lead, may be relatively straight when the inner element is positioned totally in the tubular element. However, when the distal end of the tubular element is withdrawn so that the distal end of the inner element protrudes from the distal end of the tubular element, the electrode lead may take a corresponding curvature. Thereby, the curvature of the distal end of the electrode lead can be precisely controlled.

According to still another embodiment, the tubular element has a pre-set curvature. This embodiment is an alternative to the previous embodiment. According to this embodiment, the inner element is preferably stiffer than the tubular element. Thus, when the inner element is withdrawn, the tubular element causes the electrode lead to bend according to the pre-set curvature of the tubular element.

According to still another embodiment, an arrangement is provided that one end of the member for preventing the end of the guide wire from passing said end of the member.

DESCRIPTION OF THE DRAWINGS

FIGS. 3 and 4 show different embodiments of a cross-sectional view of the inventive member, taken along line B—B in FIG. 2.

FIG. 5 is a schematic cross-sectional view of a guide wire in a member in accordance with the invention.

DESCRIPTION OF THE PREFERRED EMBODIMENTS

Figure 1:
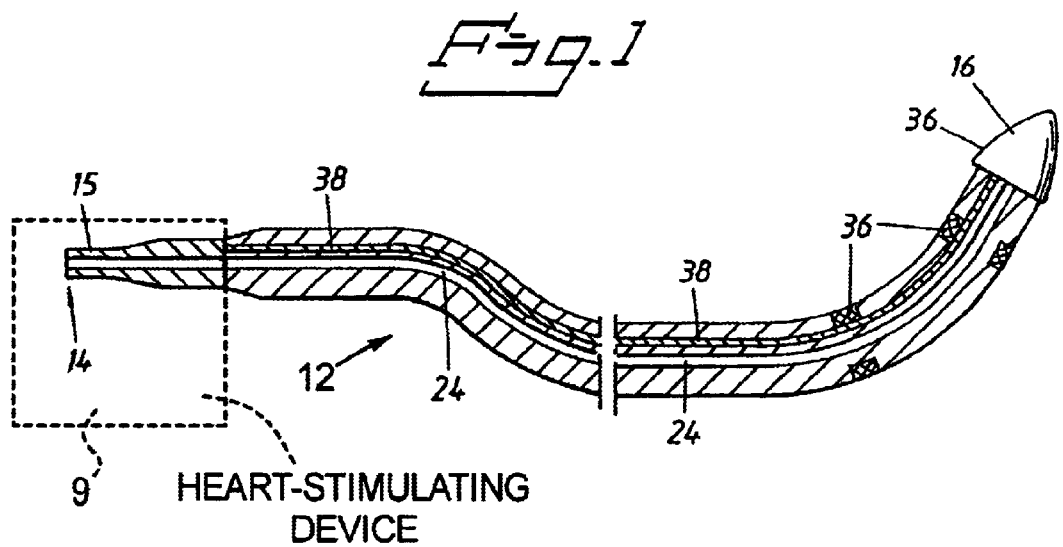
FIG. 1 is a schematic illustration of a cross-sectional view of a heart electrode lead in which the invention is usable.

Since a heart electrode lead is well known in the art, the heart electrode lead 12 is only shown schematically in FIG. 1. This figure, therefore, does not include all the details of such an electrode lead 12. The electrode lead 12 is of the kind which is adapted for insertion via the vascular system into the human or animal heart. The electrode lead 12 has a proximal end 14, which is adapted to be connected to an implantable heart-stimulating device 9 (schematically indicated with a dashed outline). The proximal end 14 has a connector tip 15, which preferably is of a standard dimension in order to be connected to the heart-stimulating device. Preferably, this connector tip 15 has a dimension according to the international standard IS-1, but also other dimensions which exist in this technical field are possible. The heart-stimulating device may, for example, be a pacemaker or a defibrillator. The heart electrode lead 12 also has a distal end 16 with one or more electrode surfaces 36 and adapted to be inserted into the heart. The electrode surfaces 36 are used to sense signals from the heart or to deliver signals to the heart. The electrode lead 12 has a channel 24, which extends from the proximal end 14 to a position at or close to the distal end 16. The electrode lead 12 also has one or more electrical conductors 38, which extend along the electrode lead 12 and which are adapted to electrically connect the heart-stimulating device to the electrode surfaces 36. The electrical conductor or conductors 38 are only schematically indicated in FIG. 1. According to a preferred embodiment, such conductors 38 are wound such that they extend around the channel 24. In the channel 24, a member according to the present invention and/or a guide wire arrangement may be positioned. It should be noted that a guide wire is sometimes also called a stylet. Such a guide wire, or stylet, may comprise one or two elements.

Figure 2:
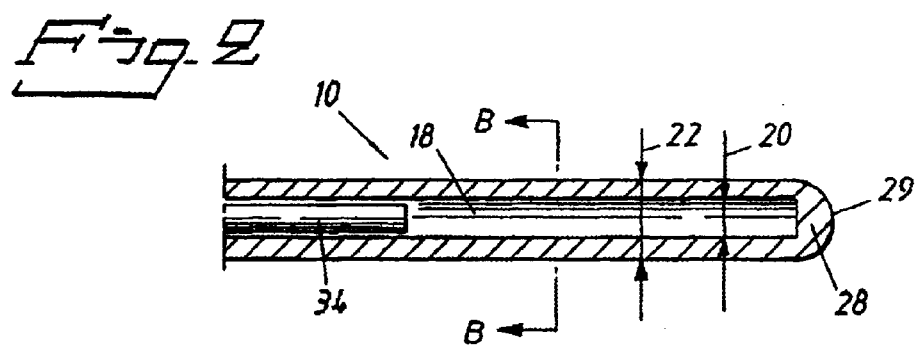
FIG. 2 is a schematic cross-sectional view of a member for modifying the stiffness of the heart electrode lead of FIG. 1, in accordance with the principles of the present invention.

FIG. 2 shows a schematic representation of the stiffness-modifying member 10 according to the present invention. The member 10 has preferably a tubular shape. The member 10 is flexible, elongated and has a longitudinal cavity 18 extending along the member 10. The member has an interior cross-sectional dimension 20 defined by the cavity 18. The member 10 also has an exterior cross-sectional dimension 22. The exterior cross-sectional dimension is such that the member can be introduced into the channel 24 of the heart electrode lead 12. This means that the exterior cross-sectional dimension 22 is such that the member 10 can be introduced via the proximal end 14 of the heart electrode lead 12.

The interior cross-sectional dimension 20 is dimensioned such that a guide wire 34 may be movably arranged in the cavity 18. The guide wire 34 may thus be pushed forward in the cavity 18 such that it extends to a position at or close to the distal end 29 of the member 10. Preferably, arrangement 28 is provided at the distal end 29 of the member 10 in order to prevent the end of the guide wire 34 from passing the end 29 of the member 10. The arrangement 28 may simply be a plug so that the cavity 18 does not extend all the way to the distal end 29 as shown in FIG. 2. The distal end 29 of the member 10 may be shaped such that the member 10 can be easily pushed forward in the channel 24 in the electrode lead 12. It is also possible that the distal end 29 of the member 10, or the whole outer surface of the member 10, is coated by some material which reduces the friction between the member 10 and the channel 24. The stiffness-modifying member 10 may be made in any suitable material. Preferably, a non-metallic material such as a polymer is used. One advantageous possibility is to produce a plurality of members 10 made of slightly different materials such that the different members 10 have different stiffness. Thereby, a suitable member 10 of a specific stiffness can be used in the electrode lead 12 depending on the needed flexibility of the electrode lead 12 for a specific use.

The member 10 can be constructed to have built-in tension such that the member 10 has the pre-set curvature. For example, it is sometimes advantageous that the distal portion of the member 10 has such a pre-set curvature. Thereby, the distal portion of the electrode lead 12 can be positioned at a predetermined location in the heart. In case the member 10 has a pre-set curvature, a guide wire 34 without any pre-set curvature is preferably used. Thereby, the member 10 can be kept straight by the guide wire 34. When the guide wire 34 is withdrawn, the distal portion of the member 10 is bent according to its pre-set curvature.

Figure 3:
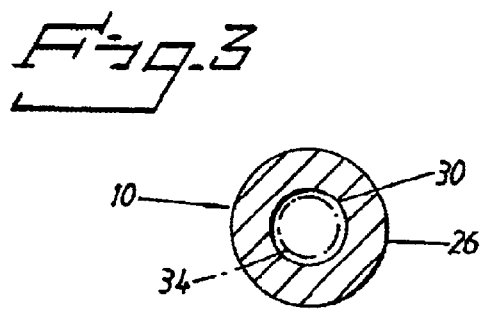

FIG. 3 schematically shows a cross-section taken in the direction B—B in FIG. 2. The outer boundary 26 of the cross-section of the member 10 is essentially circular. The longitudinal cavity 18 in the member 10 has an essentially circular cross-section 30. Thereby, the cavity 18 is adapted to allow a guide wire 34 having a corresponding circular outer boundary to be movably arranged in the cavity 18.

FIG. 4 shows a similar cross-section as FIG. 3. In the embodiment of FIG. 4, the member 10 has a longitudinal cavity 18 with an elongated cross-section 32. Thereby, the cavity 18 is adapted to allow a guide wire 34 having a corresponding elongated cross-section to be movably arranged therein. Such a guide wire 34 is particularly suitable when the electrode lead 12 is supposed to be more flexible in certain bending direction than in another.

FIG. 5 schematically shows a cross-section of a guide wire arrangement 40. This arrangement 40 is adapted to be movably positioned in a channel 24 in an elongated heart electrode lead 12 of the above-described kind. The guide wire arrangement 40 comprises a stiffness modifying member 10 of the kind described above and an elongated guide wire 34 movably arranged in the longitudinal cavity 18 of the member 10. The guide wire 34 may be a single elongated element. The guide wire 34 may also, as shown in FIG. 5, have two elements: an outer elongated tubular element 42, which is movably arranged in the longitudinal cavity 18 of the member 10, and an inner elongated element 44, which is movably arranged in the tubular element 42. The inner element 44 may have a pre-set curvature, such that the distal portion of the member 10, and thereby the distal portion of the electrode lead 12, is bent according to the pre-set curvature when the tubular element 42 is withdrawn from the distal end of the inner element 44. Alternatively, the tubular element 42 may have a pre-set curvature, such that the distal portion of the element 10, and thereby the electrode lead 12, is bent according to the pre-set curvature when the inner element 44 is withdrawn from the distal end of the tubular element 42. As is also shown in FIG. 5, the member 10 is provided with arrangement 28 for preventing the end of the guide wire 34 from passing the distal end 29 of the member 10. It is also possible that the member 10 and the guide wire 34, or one of the guide wire elements 42, 44 if a double guide wire is used, have different pre-set curvatures. By manipulating the guide wire 34 and the member 10, the distal portion of the electrode lead 12 may be caused to bend in different directions. Thereby, the shape of the distal portion of the electrode lead 12 may be modified during the insertion phase of the electrode lead 12 into the body.

It should be mentioned that the basic idea of a double guide wire is per se known from, for example, the above-mentioned U.S. Pat. No. 5,170,787.

Suitable materials for the stiffness-modifying member 10 include fluorine-containing polymers, such as polytetrafluoroethene (sold under the trade name Teflon®). Also any other plastic material of a suitable stiffness may be used. The exterior cross-sectional dimension 22 of the member 10 is primarily limited by the interior dimension of the connector tip 15. The exterior dimension of the connector tip according to the most commonly used standard IS-1 is about 1.59 millimeters. Since the connector tip 15 has a certain thickness, the interior dimension has to be smaller than the mentioned exterior dimension. Therefore, also the exterior cross-sectional dimension 22 of the member 10 must be smaller than 1.59 millimeters. Furthermore, the interior cross-sectional dimension 20 must be large enough for a guide wire to be positioned therein. Guide wires of different exterior dimensions exist. A guide wire may, for example, have an exterior dimension of 0.41 millimeters. However, a guide wire may be specifically produced to fit in a member 10.

An example of how to use a stiffness-modifying member 10 according to the present invention is as follows. A guide wire 34 may be introduced into the cavity 18 of the stiffness-modifying member 10, such that a guide wire arrangement 40 of the above-described kind is obtained. This guide wire arrangement 40 may then be introduced into the channel 24 of a heart electrode lead 12 by pushing the guide wire 34 and thereby the member 10 in via the proximal end 14 of the electrode lead 12. The electrode lead 12 may then be introduced in, for example, a vein leading to the heart of a patient. Before the electrode 36 at the distal end 16 of the electrode lead 12 reaches its predetermined position in the heart, the guide wire 34 is withdrawn a certain distance in order to avoid perforation of the heart. The stiffness-modifying member 10, however, is not withdrawn, such that the distal portion of the electrode lead 12 maintains a certain stiffness. Thereby, the distal end 16 of the electrode lead 12 can be positioned in the heart. In other words, the electrode lead 12 maintains an appropriate flexibility. When the distal end 16 of the electrode lead 12 has been positioned at the predetermined location in the heart, the guide wire 34 and the member 10 may be withdrawn from the electrode lead. In case a certain stiffness of part of the electrode lead 12 is advantageous, the member 10 may be only partly withdrawn from the electrode lead 12. The member 10 may also be left in the channel 24, and not withdrawn at all.

According to an alternative embodiment, it is possible to arrange more than one stiffening-modifying member 10 in the channel 24 of the electrode lead 12. The member 10 may in such a case be formed of an outer tubular member and an inner tubular member arranged in the outer tubular member. By such a construction, the stiffness of the electrode lead 12 may be modified even further by withdrawing 10 one or both of such members.

Although modifications and changes may be suggested by those skilled in the art, it is the intention of the inventors to embody within the patent warranted hereon all changes and modifications as reasonably and properly come within the scope of their contribution to the art.

What is claimed is:

1. A member for use with an elongated heart electrode lead having a channel therein, said member being elongated and flexible and having a longitudinal cavity therein defining an interior cross-sectional dimension adapted to allow a guide wire to be longitudinally advanced and retracted in said cavity to cause a selected portion of said guide wire to be present in said cavity to selectively stiffen said member, and said member having an exterior cross-section allowing said member to be withdrawably positionable in said channel of said elongated heart electrode lead, and said member having an end arrangement adapted to prevent an end of a guide wire from passing through said end arrangement.

2. A member as claimed in claim 1 wherein said exterior cross-section is substantially circular.

3. A member as claimed in claim 1 comprised of a non-metallic material.

4. A member as claimed in claim 3 wherein said member is comprised of a polymer.

5. A member as claimed in claim 1 wherein at least a portion of said member has a pre-set curvature.

6. A member as claimed in claim 1 wherein said interior cross-section of said cavity is substantially circular.

7. A member as claimed in claim 1 wherein said interior cross-section of said longitudinal cavity has an elongated oval shape.

8. A heart electrode lead comprising:

an elongated lead body adapted for insertion into a living subject, said electrode lead body having a proximal end adapted for mechanical and electrical connection to a heart-stimulating device and a distal end having at least one electrode surface for interaction with cardiac tissue, and having a channel extending between said proximal end and said distal end;

at least one electrical conductor carried in said electrode lead body, and electrically connected to said at least one electrode surface;

an elongated flexible member having an exterior cross-section allowing said member to be withdrawably positionable in said channel for insertion and withdrawal relative to said channel via said proximal end, said member having a cavity therein; and a guide wire movably disposed in said cavity in said member, and being selectively insertable and withdrawable relative to said cavity via said proximal end to cause a selected portion of said guide wire to be present in said cavity to selectively stiffen said member and said lead body.

9. A guide wire arrangement for use with a heart electrode lead having a channel therein, said guide wire arrangement comprising:

an elongated flexible member having an exterior cross-section adapted to allow said member to be withdrawably positioned in said channel of said heart electrode lead, and having an interior longitudinal cavity;

a guide wire movably disposed in said cavity of said member and being selectively insertable and withdrawable relative to said cavity to cause a selected portion of said guide wire to be present in said cavity to selectively stiffen said member; and said member having an end arrangement preventing an end of said guide wire from passing through said end arrangement.

10. A guide wire arrangement as claimed in claim 9 wherein said guide wire comprises a single elongated element.

11. A guide wire arrangement as claimed in claim 10 wherein at least a portion of said guide wire has a pre-set curvature.

12. A guide wire arrangement as claimed in claim 9 wherein said guide wire comprises an outer elongated tubular element movable in said cavity of said member, and an inner elongated element movable in said tubular element.

13. A guide wire arrangement as claimed in claim 12 wherein said inner element has a pre-set curvature.

14. A guide wire arrangement as claimed in claim 12 wherein said tubular element has a pre-set curvature.

* * * * *